United States Patent [19]

McDonald et al.

[11] Patent Number: 5,039,617

[45] Date of Patent: Aug. 13, 1991

[54] CAPILLARY FLOW DEVICE AND METHOD FOR MEASURING ACTIVATED PARTIAL THROMBOPLASTIN TIME

[75] Inventors: Katheryne M. McDonald, Mountain View; Laura J. Winfrey, Belmont; Michael M. Gorin, Palo Alto; James L. Hill, San Jose; Po C. Hsu, Cupertino, all of Calif.

[73] Assignee: Biotrack, Inc., Mountain View, Calif.

[21] Appl. No.: 341,045

[22] Filed: Apr. 20, 1989

[51] Int. Cl.[5] .............................................. G01N 33/86

[52] U.S. Cl. .......................................... 436/69; 435/13; 435/810; 422/57; 422/58; 422/73; 422/81

[58] Field of Search .................... 436/69, 180; 435/13, 435/810; 422/57, 58, 68, 73, 81, 82

[56] References Cited

U.S. PATENT DOCUMENTS

| | | | |
|---|---|---|---|
| 4,672,030 | 6/1987 | Witt | 435/13 |
| 4,755,461 | 7/1988 | Lawson et al. | 435/13 |
| 4,756,884 | 7/1988 | Hillman et al. | 422/73 |
| 4,761,381 | 8/1988 | Blatt et al. | 436/165 |
| 4,849,340 | 7/1989 | Oberhardt | 435/13 |

OTHER PUBLICATIONS

Tans et al., "Properties of Sulfatides in Factor-XII--Dependent Contact Activation", *Blood* (1982), 59:69–75, No. 1.

Thomson, "The activated partial thromboplastin time", in *Blood Coagulation and Haemostatis, a practical guide* [Chapter 7], Churchill Livingston, Inc., New York (1985).

*Primary Examiner*—David L. Lacey
*Assistant Examiner*—Jeffrey R. Snay
*Attorney, Agent, or Firm*—Richard L. Neeley

[57] ABSTRACT

Methods and devices are provided for carrying out activated partial thromboplastin time (APTT) analysis on a whole blood sample to which no anticoagulant has been added by applying the sample to a capillary track contained in a housing, wherein the capillary track comprises sample entry and venting ports, at least one capillary track connecting the entry and venting ports, and reagents capable of initiating an APTT analysis, wherein clotting time is measured by the cessation of blood flow in the capillary track.

28 Claims, 1 Drawing Sheet

CAPILLARY FLOW DEVICE AND METHOD FOR MEASURING ACTIVATED PARTIAL THROMBOPLASTIN TIME

BACKGROUND OF THE INVENTION

This invention is directed to blood clotting measurements and is more specifically directed to measurements of activated partial thromboplastin time.

FIELD OF THE INVENTION

There are two principal tests used in analytical chemistry to determine the time required for blood coagulation. The first test is referred to as prothrombin time and measures the time of coagulation resulting from activation of factor VII (the extrinsic pathway). A second test, named partial thromboplastin time (PTT), measures the time of coagulation that occurs when the intrinsic pathway is activated. When PTT analyses were first being run, coagulation was initiated by contact of a blood sample with a surface, typically glass. It has been determined, however, that more reproducible results are achieved if a soluble activator is used to initiate the intrinsic pathway. The term "activated partial thromboplastin time" (APTT) has come into being to designate this type of test.

Unfortunately, the APTT test has not been standardized, and the term APTT covers a great variety of reagents and techniques in which a partial thromboplastin time is measured using an activator and the recalcification of the test plasma (the test is carried out on an anticoagulated sample containing a calcium chelator). Nevertheless, the APTT assay is one of the most widely used and valued screening tests for blood coagulation disorders. The test reflects changes in clotting factors VIII, IX, X, XI, and XII and defects in the "contact phase" (e.g., in the function of factors XI and XII, prekallikrein and high molecular weight kininogen). APTT is also prolonged if there are deficiencies in factors II, V, and fibrinogen. Furthermore, APTT is the monitoring method of choice for the effect of inhibitors of the intrinsic clotting pathway, such as heparin, which is commonly used to prevent post-surgical clotting and in various anticlotting regimens with coronary patients.

A number of problems (especially relating to complexity and irreproducibility) exist in current APTT tests which prevent patient-side measurements. APTT measurements now being carried out require a number of operations that can only be completed by skilled personnel. Currently, blood samples obtained by venipuncture are required. Samples are drawn into tubes containing an anticoagulant that binds calcium ions, such as sodium citrate. The blood must be refrigerated prior to testing because of the potential for the coagulation pathway to be activated even in the presence of anticoagulant. After collection and storage, blood plasma is usually separated from red cells and platelets by a variety of means, such as centrifugation. A precisely measured volume of plasma is then mixed with exact amounts of (a) a negatively charged activating reagent (e.g., ellagic acid) and (b) a phospholipid mixture (referred to as partial thromboplastin). The mixture is then incubated for a defined time (typically 2-5 minutes), and the clotting reaction is initiated by addition of an exactly measured quantity of a reagent containing calcium ions, which reverse the effect of the exogenous anticoagulant. Clotting time is then measured by some physical means, such as light scattering. The delay required for transport of samples to the laboratory, sample pre-treatment and assay causes significant risk to patients who are in immediate danger of hemorrhage or thrombosis if, for example, they are being treated with inappropriate levels of heparin.

While this technique for measurement of APTT is precise for a single plasma sample in the hands of skilled users, it is not suitable for patient-side use by unskilled workers or patients. A particular problem that arises when the test is done at a site remote from the patient is that exposure of the sample to elevated temperature or mechanical insult for uncontrolled periods of times causes significant variation in the test results. Additionally, assay calibration error and variability cause significant variations in conventional assays.

U.S. Pat. No. 4,756,884, describes an integrated device containing a predispensed, dry reagent in a capillary track that can be used to measure clotting of blood samples. While it is possible to use the cartridge described in this patent to carry out a APTT test that gives a useful result, room for improvement in dynamic range, reliability and convenience remain.

SUMMARY OF THE INVENTION

Accordingly, it is an object of the present invention to provide an improved capillary flow device and method for carrying out an APTT analysis on a blood sample.

It is a further object of this invention to provide the capability of carrying out an APTT analysis on a sample to which no anticoagulant has been added.

It is yet another object of this invention to allow analysis of whole blood obtained from capillaries, as opposed to venous blood, in order that samples can be obtained without venipuncture.

It is also an object of this invention to provide an APTT analysis result without preincubation of sample with reagent while using a small (preferably less than 40 μl ), unmeasured sample of whole blood.

These and other objects of the invention as described hereinafter will become more readily apparent have been accomplished by providing a device useful for determining activated partial thromboplastin time in a blood sample comprising, in a housing, a continuous capillary track comprising an inlet port, at least one capillary unit acting as the motive force for moving the fluid medium in the device, and a venting port, wherein said capillary track further contains a reagent capable of initiating blood clotting, wherein the reagent is a mixture of (1) an activating agent for activated partial thromboplastin time measurements and (2) a mixture of phospholipids in amounts sufficient to initiate clotting, said amounts being selected to provide a time of flow stoppage that is essentially independent of blood hematocrit. In the method used with the device, a blood sample is introduced into the entry port of the device, the sample is allowed to transit the capillary track by capillary action, and activated partial thromboplastin time is determined from the time required for blood coagulation and flow stoppage in the capillary track. In preferred embodiments the device provides a capillary track that allows continuous flow of whole blood in the absence of the reagent for at least 200 seconds, preferably maintaining continuous flow using no more than 40 μl of sample. The method is typically carried out on a whole blood sample, as opposed to plasma sample previously used, and can be carried out on capillary blood, such as that which can be obtained by a finger stick, without intervening treatment.

BRIEF DESCRIPTION OF THE DRAWINGS

The invention will be better understood by reference to the following detailed description of specific embodiments when considered in combination with the accompanying drawings which form part of the specification, wherein.

DESCRIPTION OF THE SPECIFIC EMBODIMENTS

Figure 1A:
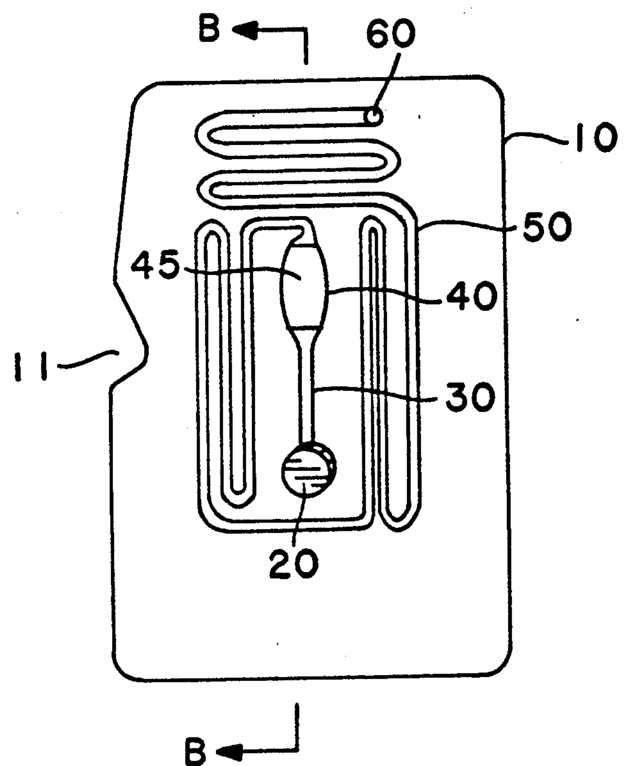
FIGS. 1A and 1B are plan and cross-sectional views of one embodiment of the subject invention.

This invention provides devices and methods, where the devices rely upon capillaries, chambers, and orifices to pump fluids; to control measurement of fluids, reaction times, and mixing of reagents; and to determine a detectable signal. In particular, the devices and methods of the present invention are directed to analyses for activated partial prothrombin time. By using the device specifically described in the present application, APTT measurements can be carried out on whole blood samples without requiring the use of any anticoagulant. Additionally, capillary blood (rather than venous blood) can be used, and the assay can be carried out on a blood drop using a sample volume as small as 20 μl.

The general characteristics of a capillary flow device of the type used in the present invention are described in U.S. Pat. No. 4,756,844. However, the device and method of the present invention differ from the device and method of the patent and represent improvements thereover. Specifically, the APTT device of the present invention comprises, in a housing, a continuous capillary track containing the reagents necessary for initiation of the APTT test and comprising a sample entry port, at least one capillary unit acting as the motive force for moving the blood sample in the device, and fluid venting means to allow exit of air in order that capillary flow can take place. In particular, the capillary track allows continuous flow of whole blood in the capillary track (in the absence of the APTT reagents) for at least 200 seconds, preferably at least 400 seconds, using no more than 40 μl of sample. The reagent utilized in the capillary track is a mixture of (1) an activating agent (a soluble, negatively charged polymer) for activated partial prothrombin time measurements and (2) a mixture of phospholipids.

The method comprises introducing a blood sample into the entry port of the device. The blood sample can be used without pretreatment (e.g., such as with anticoagulants) if the device and reagent formulation follow the preferred embodiments set forth below. Whole blood is preferred, especially capillary blood, such as can be obtained by puncture of surface capillaries in a finger (a "finger stick") or earlobe. When the patient is an infant, heel sticks are sometimes used. Blood can be subjected to physical and/or chemical treatments, if desired, although such treatments are not preferred. Typical physical treatments include filtration or centrifugation to remove red blood cells (preparation of a plasma sample), maintaining a constant temperature of the sample during storage (e.g., in a water bath), or cooling of the sample (e.g., by refrigeration). Typical chemical treatments include addition of anticoagulants (e.g., calcium chelators, such as EDTA, or heparin), addition of diluent, and addition of one or more reagent that affects the clotting reaction that is being measured (e.g., addition of a blood clotting factor to a sample to determine if that factor is the limiting factor in the clotting reaction).

After the sample is added to the entry port, it is then allowed to transit the capillary track by capillary action, whereby the sample contacts the reagent. The partial thromboplastin time is determined from the time required for blood coagulation to occur, resulting in flow stoppage in the capillary track.

The capillary track of the present device can be a uniform capillary track but normally comprises a number of segments having different purposes. Some of the regions of the track are referred to as chambers because they have a substantially larger cross-section or diameter in one direction transverse to the direction of flow than do other narrow regions of the capillary track, which are referred to as channels. The cross-section or length in the direction of flow of specific regions may be similar or may differ by a factor of ten or more depending on the function of the various capillary channels and chambers. Capillary channels will usually have maximum diameters in the range of about 0.005 mm to 1 mm, usually about 0.05 mm to 0.5 mm. Capillary chambers usually have one diameter in this range to provide for capillary flow.

In some embodiments, provision can be made for larger incubation by providing for delayed flow. Sealable venting parts, dissolvable dams, and other techniques for providing for temporary cessation of sample flow are discussed in U.S. Pat. No. 4,756,988.

Most embodiments of the invention will have an entry port, an initial capillary channel leading to a chamber region containing reagents, and a long narrow capillary channel leaving the reagent chamber to provide for the necessary flow time. The length of the capillary track, particularly the first capillary channel, more particularly the first capillary when it is joined to the entry port, will be at least about 2 mm, more usually at least about 5 mm, and may be 1 cm or more, usually not more than about 2 cm, preferably not more than 1.5 cm while subsequent capillaries may be shorter or longer, frequently at least one being longer, to provide the extended capillary flow required for APTT testing. The first capillary channel usually has a height in the range of from 0.05 to 0.175 mm, preferably from 0.05 to 0.125 mm, especially about 0.07 to 0.085mm. The width of the channel can vary in preferred embodiments from about 0.05 to about 3 mm, preferable from about 0.75 to about 2 mm, especially about 0.8 to 1.2 mm.

The first capillary serves to connect the entry port to the reagent chamber and is normally the location at which flow is measured. It will also initially control the rate of flow into the reagent chamber, although flow is eventually controlled by the long flow track leaving the reagent area once sample reaches this track. Other components which may affect the rate of flow in the chamber include baffles, walls or other impedimenta in the chamber, the geometry of the chamber, the reagent in the chamber, and the nature of the surfaces in the capillary and chamber.

The capillary control and use of relatively thin heat conductive walls allows for rapid heat transfer. In addition, the thin capillaries permit optical measurements of flow, particularly based on transmission of light, with optically dense samples, e.g., whole blood.

The capillarity of the capillary track provides essentially all of the driving source for the movement of liquid through the device. Accordingly, careful fabrication of the capillary track to exact dimensions is required. The device is normally employed in the horizontal position, so that gravity does not significantly affect the flow rate. The composition of the walls of the capillary are selected so as to provide the desired degree of wetting and surface tension or the walls are modified to provide the desired physical properties. The device is usually employed without ancillary motive force, such as pumps, gravity or the like.

The chambers also have a variety of functions, serving as protection for the reagent(s), mixing chambers for dissolution of reagent and/or reaction with reagent, volume measurement, incubation, and the like. The chambers will be primarily employed for mixing of reagents with sample and to provide a relatively large surface to which reagent can be applied during the manufacturing process. Providing a large surface area allows use of a thin coat of reagent that can be rapidly and completely dissolved and/or resuspended. A reagent chamber will typically have a rectangular or oval shape having a length of from about 2 to about 20 mm, preferably about 5 to about 15 mm, especially about 10 to 13 mm. The width is typically from about 2 to about 10 mm, preferably about 3 to about 8 mm, especially about 4 to 7 mm. The height of a reagent chamber has the same typical and preferred heights as that of the first capillary channel, as discussed above.

Depending upon the particular system, the length of the capillary channels, their cross-sectional area, the volumes of the various chambers, and their length and shape may be varied widely within the constraints discussed below. One constraint on each of the capillaries is the necessity for their function providing capillary pumping action for flow. Therefore air leaks in the space surrounding the capillary (except for designed access ports) cannot be tolerated. In order to provide for capillary flow of sufficient duration to carry out an APTT analysis on a single drop of blood, severe constraints are placed on the portion of the capillary track responsible for continuous flow during the APTT assay, referred to here as the capillary flow unit. The volume of this unit must be quite small to allow flow to continue from a single drop of blood (with a volume of no more than 40 μl preferably no more than 25 μl for the necessary time, which would be at least 40 sec, preferably at least 400 sec to allow for clinically relevant variations in APTT. Accordingly, the total volume of the capillary track should be no more than 40 μl preferably no more than 30 μl. This is accomplished by providing an introductory capillary channel and chamber with a total volume of no more than 15 μl, preferably no more than 10 μl, and a capillary flow unit exiting the reagent chamber with an initial cross sectional area of no more than 0.09mm$^2$ preferably no more than 0.03 mm$^2$ The length of the capillary flow unit is at least 200 mm, preferably at least 300 mm. It will be appreciated that the total capillary track in the device can be much longer and have much larger total volumes since proper operation of the device does not require (and indeed does not prefer) that the capillary track be completely filled by sample at any time. In normal operation, only a portion of the long capillary track leaving the reagent chamber will fill with sample before the blood sample clots and flow stops.

The exceeding small capillary tracks used in preferred devices of the invention create severe viscosity problems as blood flows through the capillary track. Accordingly, it is preferred to provide a capillary flow unit that provides for relatively constant blood flow (measured as blood leaves the entry port and enters the capillary track) in which the cross sectional area of the capillary flow unit exiting the reagent chamber increases in the direction of flow. Techniques for modifying cross sectional areas of capillary tracks to permit constant fluid flow are described in U.S. Pat. 4,756,884.

In a circular capillary of constant radius, the flow rate is equal to $$\frac{\pi R^4 \Delta P}{8 \mu L}$$

where R is the radius, ΔP is the driving force due to capillary pressure, μ is the fluid viscosity, and L is the filled capillary length.

All other parameters remaining constant, as a capillary fills (L increases) the flow rate decreases continuously.

In the present invention, the capillary is actually a number of resistances in series, and it can be shown that increasing the radius along the capillary length the rate of decrease of flow rate is lessened. In this way, the flow rate remains more constant throughout the assay than it would otherwise. This effect holds despite the slight decrease in capillary pressure (ΔP) that results from increasing R.

An additional problem resulting from the small diameter of the capillary track relates to the process by which such tracks are manufactured. Since the device is intended for clinical analysis, a manufacturing process must be available that minimizes discrepancies between devices manufactured at different times. The commercial embodiment of the device described in U.S. Pat. No. 4,756,884 is a PT test device known as a Protime cartridge and is manufactured by Biotrack, Inc. of Mountain View, Calif. This device is manufactured by ultrasonic welding of two plastic plates having grooves in their surfaces that form the capillary tracks when the two plates are welded together. The tolerances required by the smaller capillary track of the APTT device are difficult to achieve in the same manner.

However, suitable tolerances are achieved if modifications are made to the molding and welding procedures. Instead of providing two semicircular grooves in opposing plates that are welded together, as in the PT test device, a single groove is provided in one of the two plates used to make the APTT device by ultrasonic welding. The second plate is flat in the area where the capillary flow unit will be formed when the two plates are welded together.

Obviously, variations in the design of the individual chambers and channels can be provided. The designs and channels will be selected to provide for optimum sensitivity for particular assays. The volumes of the chambers will be chosen so as to accommodate an appropriate sample volume. The reaction initiated in the reagent chamber will result in coagulation which produces a blockage in the capillary flow unit.

It is evident that any type of capillary channel may be employed which provides for accommodating the appropriate volume and time period to flow stoppage. Various designs for increasing the capillary path length in the housing may be used such as serpentine, linear, U-shaped, pleated, or the like. The channel cross-section may be circular, ellipsoid, rectangular, or combinations thereof, as well as other cross-section shapes.

When the capillary channels are formed by joining together two plates at least one of which has a surface depression that forms the channel (discussed in detail below) it will be recognized by those skilled in the ar that small "cracks" will be present at the locations where the two plates are joined. These cracks can represent an appreciable portion of the total volume of a capillary channel (e.g., 40 to 60%). The length and volume of the channels are therefore preferably determined empirically rather than by relying on calculations based on length and radius or other dimensions. Although such cracks also affect the volume of other parts of the capillary track, such as the reagent chamber, they are most important in affecting the small capillary channels.

Any of the capillary channels can be of constant or varying cross-section. With a constant cross-section, the observed flow velocity will diminish with the path length traversed. Therefore, the observed change in velocity will have two components: (1) an inherent reduction in velocity related to the increasing friction (viscous drag) with increasing fluid path length; and (2) increasing (or decreasing) viscosity of the medium due to any reaction occurring.

In order to minimize the effect of the fluid path length, a tapered capillary may be employed. The taper can be calculated by determining the crosssection, e.g., height and width, of the channel for each point along the channel path.

In a preferred embodiment of the invention, the capillary flow unit comprises a semicircular track exiting a chamber where reagent is present and continuing to the venting port. The radius of the semicircular track is from 0.05 to 0.125 mm, preferably 0.6 to 0.8 mm, especially about 0.076 mm at the beginning of the capillary flow unit (defined as the junction between the reagent chamber and the capillary unit). It is especially preferred to proved a radius that increases with distance from the reagent chamber, as discussed above. Usually the rate of increase will decrease as the track length increases (i.e., the second differential of a plot of radius vs. length will be negative). An initial constant-radius region can be provided, followed by one or more regions in which the radius varies. In one especially preferred embodiment, the radius of the semicircle is constant for the first 30 mm of the track. For the next 70 mm of the track, the radius is defined by the formula $r=0.028\times L^{1/3}$, wherein r is the radius and L is the distance from the beginning of the flow track (all distances in millimeters). From L=100 to L=120 mm, $r=0.0285\times L^{1/3}$; from L=120 to the end of the track, $r=0.029\times L^{1/3}$. This decrease in the rate at which the radius is increasing provides particularly advantageous results.

The device will be fabricated from materials with the appropriate physical properties, such as optical transmission, thermal conductivity, and mechanical properties, and which allow for uniform coating and stability of reagent, as well as medium compatibility, for example, blood compatibility. Where blood is the medium, the material should be configured to assure good blood flow stoppage or slowing once clotting is initiated. For this purpose, suitable plastics include those for high surface free energies and low water sorption, including PETG, polyester (Mylar ®), polycarbonate (Lexan ®), polyvinyl chloride, polystyrene, and SAN. A particularly preferred plastic is acrylonitrile-butadiene-styrene (ABS), particularly ABS supplied by Borg Warner under the tradename Cycolac. However, since these plastics are hydrophobic and exhibit poor reagent coating and poor blood flow, the plastics can be rendered hydrophilic by treatment with argon plasma, using a plasma etcher or by corona discharge. Suitable conditions are 10–25 watts at 13.56 MHz and one torr chamber pressure for 5–10 min. Alternatively, a protein, e.g., albumin, coating can be used in some instances by passing a solution over the upper and/or lower parts used to make the device, the solution containing about 1–5% serum albumin, allowing the solution to stand for 30 min., wiping, and drying. Other modifications may also find application. Plasma etching and corona discharge provide markedly superior flow control characteristics and reproducibility.

The device can be fabricated in a variety of ways. The receiving and reagent chambers can be formed in the plastic sheet by vacuum forming (PETG), injection molding (PETG, polystyrene, SAN), or hot stamping. Capillaries may be formed by etching a channel into the plastic. The device can be sealed by placing a cover slip (with appropriate vent holes at the inlet and vent) on the base sheet, and sealing with ultrasonic welding or by solvent bonding. Of these techniques, markedly superior products are obtained by injection molding of the plastic device in pieces so as to form a depression in at least one surface of at least one plastic piece. ABS polymers are particularly suited to injection molding and additionally provide a clear plastic which is suitable for numerous optical detection techniques. ABS polymers are also suitable for ultrasonic welding. It is preferred to form the chambers from two substantially flat plastic pieces in which the capillaries and other chambers are formed by producing matching depressions in two surfaces of two different shaped plastic pieces. It is preferred that on one of the pieces ridges, known as energy directors, completely surround the depression in a closely spaced relation so as to form a surface of first contact when the two pieces are placed together. When ABS is used, the ridges are typically 7.5 mil±0.5 mil above the surface of the plastic. The ridges are typically formed in the shape of a triangle, typically an equilateral triangle. The center of the ridge is typically 17.5±0.5 mils from the edge of the depression that will form the chamber. Use of such energy directors with ultrasonic welding produces a highly reproducible seal around the edges of the internal chamber that is formed when the two sheets are ultrasonically welded together. Access ports are typically formed by molding or drilling holes into the depressed surfaces of the individual plastic pieces prior to welding. Accordingly, the welded ridges form a complete seal around the lateral edges of the internal chambers.

While other materials may be used for fabrication, such as glass, for the most part these materials lack one or more of the desirable characteristics of the indicated materials and therefore have not been discussed. However, there may be particular situations where glass, ceramic or other material may find application, such as a glass window for optical clarity, modification of surface tension, and the like.

The flow in the capillary channel unit can be detected by various techniques which allow for detection of fluid flow, e.g., flow sensors or pressure sensors, or by having a detectable component in the assay medium, which can be detected visually or by optical means. Techniques which allow for fluid flow determinations include the use of means for measuring triboelectricity, means for detecting the rate of passage of liquid, detecting Doppler effects, or the like. Preferably, a component is used in the medium (either in the sample or added as an additional component either prior to application of sample to the device or by including the component in an early portion of the capillary track) which allows for flow detection by detecting the passage of the component through the first capillary channel exiting a receiving chamber.

When the fluid flowing through the device contains particles, flow can be detected by the creation of a speckle pattern resulting from the movement of the particles in the capillary track, preferably the first capillary channel, and the passage of a coherent light source, e.g., laser beam, or an LED, through the capillary track. A speckle pattern results from the interaction of particles and coherent light. Flow (motion) of the particles makes the speckles move with a frequency associated with the flow rate and the light or speckle fluctuations can be detected by a photodetector. The photodetector can be designed to detect an area either larger or smaller than about the size of a speckle, preferably about 10 to 100 times the size of a speckle. A plurality of photodetector elements may be employed for detecting different areas and averaging the signals from each area. The speckle pattern can also be used to determine the size of the particles by analysis of the size of the speckles.

By employing a photodetector, the change in the light pattern as a result of a change in the rate of flow can be determined by appropriate electronic means, such as photodiodes or phototransistors, which would feed the electrical signal resulting from the fluctuating light to an appropriate circuit. Particularly easy to distinguish is a flowing liquid from a stationary liquid. Thus, the slowing or stoppage of flow can be readily detected and the change in rate of flow or the time of passage through the first capillary can be determined from the beginning of flow to the stoppage of flow.

A preferred method for measuring a speckle pattern uses a semiconductor laser and photodetector. By exposing a photodetector of sufficiently small area to a speckle pattern, a random signal (noise) is observed. The average of the random signal observed as a DC signal is inversely proportional to the red cell density, and changes in the fluctuation continues until flow stoppage, e.g., clotting, occurs. Such apparatus may include a housing for receiving and holding the device and means for controlling the temperature.

As the area of the photodetector is increased in relation to the speckle size, the ratio of the desired random noise signal to the average DC signal is reduced. However, a larger photodetector area allows looser manufacturing assembly tolerances. It is therefore possible to vary these parameters to provide a number of acceptable values suitable for manufacture of a working detector.

In addition to useful modifications to the device of U.S. Pat. No. 4,756,884 for use in the preferred embodiments described above, modifications to the APTT reagent are also useful for preparing a commercial APTT device. In currently available APTT methods, activation and clotting processes are independent of each other. Since the device and method of the present invention utilize a single drop of whole blood added to a capillary track, activation and coagulation occur concurrently in the track. The reagent used in the present invention comprises a mixture of (1) an activating agent for activated prothrombin time measurements and (2) phospholipids. It has been found that carrying out an APTT measurement in a capillary track gives rise to problems that do not occur in APTT measurements that do not involve capillary flow or whole blood. A particular problem that has been solved by the present invention is the dependance of APTT on hematocrit in capillary flow devices. The small capillary sizes required for clinically useful measurements are affected greatly by the sample hematocrit, as show by the initial studies reported in the examples that follow. However, recognition of this problem has allowed the present inventors to provide a solution by balancing the activity of the intrinsic pathway activator and the phosphotide mixture that are used in the APTT measurement in the device of the invention.

The intrinsic pathway activator is typically a sulfatide (usually bovine) or a sulfoglycosylsphingolipid. Sulfatides, also known as cerebroside sulfates, are substances known to be present in mammalian tissues and cell membranes that show procoagulant activity that can be attributed to contact activation reactions. Typical (currently used) APTT methods include a preactivation or incubation step to obtain a result that demonstrates good sensitivity to deficiencies in intrinsic pathway factors and heparin. Typical activators are kaolin, silica, diatomaceous earth, ellagic acid, and glass particles. Typical phospholipid mixture extractions are prepared from rabbit brains, rabbit lungs and soybean phospholipids. Reagent formulation was optimized with capillary dimensions to result in an APTT method without preincubation that maintains good sensitivity to intrinsic pathway factors and heparin. For a discussion of the properties of sulfatides and their properties as factor-XII dependent contact activation activators, see Tans and Griffen, *Blood* (1982) 59:69, and Fujikawa et al. *Biochemistry* (1980) 19: 1322. Sulfoglycosylsphingolipids and their properties as activators are discussed in Chapter 5 "Lipid Involvement in Contact Activation," by G. Tans & J. Rosing, from the book *Coagulation and Lipids*, editor Robert Zwaal, CRC Press, Inc., Boca Raton, Flor.

The phospholipid component of the reaction mixture is preferably soybean phospholipid type II-S, although other phospholipids, such as ethanolaminephosphoglycerides (cephalins) cholinephosphoglycerides (lecithins), and phospholipid extracts of mammalian brain, lung, or platelets, can also be used. The two components, activator and phospholipid, must be present in appropriate proportions in order to achieve the desired results. When using a sulfatide or sulfoglycosylsphingolipid as the activator, the activator is typically present at 0.1 to 1 times the weight amount of the phospholipid, preferably about 0.5 times the weight amount of the phospholipid. Balance is achieved by measurement of dose-response relationships to blood clotting factors and heparin as a function of hematocrit. A compromise is made between maximized slope of the dose-response and minimal change of APTT with hematocrit. Samples for such experiments can be prepared from mechanical mixtures of red blood cell and plasma.

The activator and phospholipid mixture amounts that provide the most independence from variation with differing hematocrit are best determined empirically, using the information provided in Table 1 and Example 2 below as guidance for selection of initial amounts of reagents. The amounts of the two components are then adjusted individually to obtain the minimum dependance on hematocrit, as shown in Example 2 (see Table 5). APTT cartridges are then prepared containing the empirically determined amounts of reagent. When the cartridge design is modified from that used with a particular set of reagent amounts, it is best to redetermine the amounts of reagents.

In addition to the two essential components, other components can be present in the reagent formulation. Typically rehydration and bulking additives are present as well as buffer, spreading agents, stabilizing agents, and/or preservatives. Dyes can also be present in the formulation for use during the manufacture of the cartridge so that a quality control check can be carried out to determine whether reagent has been added to the cartridge. An exemplary formulation and a number of variations are set forth in Table 1 below.

TABLE 1

| Component | Preferred | APTT Reagent Formulation* Exemplary Composition | Range of Possible Compositions | Alternative Ingredients |
|---|---|---|---|---|
| Intrinsic Pathway Activator | Sulfatides (bovine) or Sulfoglycosil-sphingolipid | 0.4 g/L | 0.04 g-4.0 g/L | Ellagic acid, Silica, Kaolin Factor $XI_a$ |
| Substitute for Required Platelet Factor 3 | Soybean Phospho-lipid Type II-S | 0.8 g/L | 0.1-4.0 g/L | Glass, Extracts of Rabbit Brain Cephalin, Rabbit Lung Cephalin, Human Brain Cephalin; Lecithin; Platelet extract |
| Rehydration/ Bulking Additive | Polyethylene Glycol 3000-3700 MW | 7 g/L | 3-9 g/L | |
| | Sucrose | 25 g/L | 15-35 g/L | Trehalose Dihydrate, Mannose, Fructose, and other sugars |
| | Glycine | 15 g/L | 5-20 g/L | Lysine, Alanine, Hydroxyproline |
| Spreading Agent | Porcine Skin Gelatin | 10 g/L | 0-20 g/L | Fish Gelatin, Calf Gelatin, Collagen, Gum Hydroxypropyl Methyl Cellulose |
| | Triton ® X-100 | 0.1 ml/L | 0.05-0.4 ml/L | Tyloxapol, Pluronic L61, other Triton ® surfactants |
| Dye for Cartridge Inspection | Sulforhodamine B | 0.2 g/L | 0-0.4 g/L | Methyl Orange, Chlorophenol Red |
| | Bromophenol Blue | 0.2 g/L | 0-0.4 g/L | Brilliant Blue, Evans Blue |
| Stabilizing Agent | Bovine Serum Albumin | 2.5 g/L | 0-5 g/L | Other proteins |
| | N-[2-Hydroxyethyl] piperazine-N[1]-[2-ethanesulfonic Acid] (Hepes Buffer) | 1.3 mM | 0-10 mM | Sodium Barbital, Imidizole, CHAPS |
| Preservative | Thimerosal | 50 mg/L (.005%) | 0-100 mg/L | Sodium Azide, Neomycin, Sulfate, Chloramphenicol, Streptomycin, other bacteriocides |
| | Phenol | 0.5 g/L (0.5%) | 0-3 g/L | |

*Amounts of reagents are given as concentrations in a liquid formulation. An aliquot of the formulation (3 μl) was applied to a reagent chamber of the device shown in FIG. 1 and dried prior to use. See Example 1 for a description of preparation of the cartridge.

In order to eliminate the handling of reagents by the user of the device and to stabilize the reagents, the APTT reagents are supplied within the device, where by mixing with the reagents occurs in the device. The reagents may be present either diffusively or non-diffusively to the surface of the device, that is, adhered, absorbed, adsorbed or covalently-linked so that the reagent may become dissolved in the fluid or may remain fixed to the surface. Where the reagents are diffusively bound (non-covalently and weakly bound), a variety of situations can be accommodated. One situation is where the liquid front dissolves all of the reagent, so that the liquid front receives a high concentration of the reagent and most of the reaction occurs at the liquid front. A second situation would be with an excess of a reagent of limited solubility. In this situation, the reagent may be present in the liquid medium at a substantially uniform concentration. A third situation is to have a deficiency of a reagent of limited solubility, so that only the early portion of the fluid will have a relatively constant reagent concentration. Preferred is to disperse a liquid containing the dissolved reagents onto the surface of a reagent chamber. The liquid is spread over the chamber surface and dried under low humidity air.

In order to assure the reproducibility of distribution, various techniques may be employed for introducing the reagent into the chamber. Where the device is produced as two parts which fit together, the reagent may be sprayed, painted, introduced into the chamber as a liquid, lyophilized or evaporated, adsorbed, covalently conjugated, or the like. The active reagent may be combined with various stabilizers, excipients, buffers or other additives involved with the reaction.

To enhance mixing, various mechanical or ultrasonic means may be employed to agitate the sample and reagents, where the mixing means may be internal or external. Vibrators, ultrasonic transducers, magnetic rods or other mechanical mixing means, flow disrupters, mixing baffles or barriers, flow directors, or the like, may be employed. The particular manner in which agitation is provided, if provided, will vary widely depending upon the degree of agitation needed, the design of the device, and the like.

The reagent need not be coated or bound to the surface of the device, but may be provided as a soluble sponge or gel or alternatively, absorbed onto an insoluble sponge, membrane, paper (e.g., filter paper) or gel which is introduced into the reaction unit. In this manner the fluid may pass through the foam structure dissolving the reagent so as to form the reaction mixture.

The reagent may be provided in liquid form in microcapsules. The liquid reagent could be released from the microcapsules by applying pressure to the walls of the reaction unit, resulting in breaking of the microcapsules and releasing the liquid reagent.

In performing the assay, a sample would be taken and treated as may be appropriate. Blood for example might be diluted and various reagents added, particularly where there is an interest in the determination of a particular clotting or anti-clotting factor. The reagent in the device may also be altered or augmented so as to measure particular specifications of the clotting pathways (e.g., one particular component of the clotting cascade).

Once the various materials are mixed to form the sample medium, the sample medium would be introduced into the receiving unit and transferred by capillary action into the next unit. Either visual evaluation of the flow rate change or an electromechanical evaluation may be employed. The initiation of flow through the first capillary channel or through a successive capillary channel may be selected as the initiation time for measurement, or some point in between. As already indicated, various means may be employed for determining the flow velocity or time to flow stoppage.

Figure 1B:
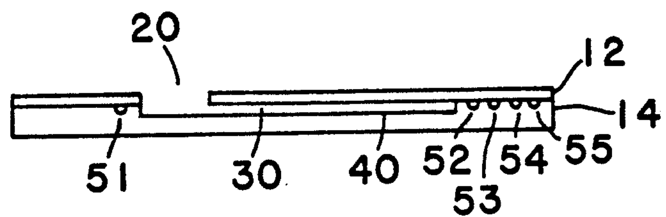

The invention will now be described with reference to the drawings in which like numbers refer to the same structures in different views of an embodiment. As shown in FIG. 1, the device comprises a housing which may be configured to be introduced into a instrument for assay determination. For example, notch 11 in housing 10 is provided to allow retention of the device (e.g., by a spring-activated catch) in the instrument in which the analysis will be carried out. The housing will be constructed so as to ensure sufficient mechanical stability to withstand mechanical handling and provide for the necessary characteristics for flow of the assay medium and detection of the detectable signal. Entry port 20 is provided for access of a blood sample to the internal capillary of the device. A first capillary passage 30 transports blood to reagent chamber 40 containing reagent 45. In the embodiment shown, housing 10 is provided with clear surfaces at the location of capillary 30 in order that this section of the capillary track can be utilized to measure movement (and cession of movement) of blood using a speckle-pattern detector as previously described. Blood sample, now mixed with reagent 45, exits chamber 40 and enters capillary flow unit 50, which connects chamber 40 to vent 60. Capillary flow unit 50 is a long, convoluted capillary pathway that provides sufficient path length for flow to be sustained for at least 200 seconds in order that an APTT measurement can be made.

A cross sectional view of the embodiment shown in part A of FIG. 1 is set forth in part B of the Figure. This cross sectional view is taken along the lines B—B shown in part A of the Figure. The construction of housing 10 from two plates, 12 and 14, is evident in this cross-sectional view. Plate 12 is essentially a flat plate that has been welded onto plate 14, which contains grooves and other depressions in its upper surface that will form the internal chambers and capillaries of the device. The two plastic pieces 12 and 14 have been welded together after being properly aligned (e.g., placed in register). "Registration" is used here in the sense of referring to proper alignment of the depressions present in the surfaces of the two pieces that are used to form the internal chambers and capillaries. Proper registration can be aided by injection molding the two pieces to provide projections on one piece that fit into holes or depressions (other than capillary- or chamber-forming depressions) in the second piece.

A single convoluted depression used to form capillary channels and chambers is present in the surface of plate 12. The cross-sectional view shown in FIG. 1 cuts through the depression at six separate locations, some of which (51, 52, 53, 54, and 55) are part of the capillary flow unit 50, while the remaining location will result in the formation of the larger initiation capillary 30 and reaction chamber 40 when plates 12 and 14 are welded together.

The following examples are provided for purposes of illustration only and are not intended to limit the invention unless so specified.

EXAMPLE 1

Comparison of Cartridge Design Characteristics

Several test cartridges were manufactured in an attempt to provide a cartridge having the characteristics necessary for carrying out an APTT test. All cartridges had an entry port comprising a 6 mm diameter hole in the top plate, a 9 mm long, 0.127 mm wide, and 0.976 mm deep first capillary track, and an oval reaction chamber (a axis =4.5 mm, b axis =10.5 mm, depth =0.076 mm). See FIG. 1.

Cartridge 1 used a cartridge flow unit exiting the reagent chamber (in this example referred to as the "track") 225 mm in length and having a full circular cross section that was prepared by welding together two plates substantially as shown in FIG. 1 but in which a depression was present in both plates in order that the circular cross section could be obtained. The track had an initial radius of 0.76 mm for 30 mm. The next region of the track had a radius defined by the formula $R=0.028\times L^{1/3}$ mm, where R is the radius of the track and L is the distance in mm along the track measured from the point at which the track exits the reaction chamber. Calculated volume of the track was 19 μl; the empirically measured volume (which includes the "cracks" between the two plates) was 34 μl.

Cartridge 2 was identical to the first but used a half circle cross section formed only in the bottom plate. Calculated volume of the track was 13 μl; the empirically measured volume was 26 μl.

Cartridge 3, which is a cartridge within the scope of the present invention, was similar to the second cartridge but used a 305 mm track length and provided for a radius that increased at a faster rate in order to minimize the flow rate decrease (prior to coagulation). For $L=0$ to $L=30$ mm, $R=0.076$ mm. For $L=30$ to $L=100$ mm, $R=0.028\times L^{1/3}$ mm. For $L=100$ to $L=120$ mm, $R=0.0285\times L^{1/3}$ mm. For $L=120$ to the end of the track, $R = 0.029 \times L^{\frac{1}{3}}$ mm. The calculated volume of the track was 17 μl; the empirically measured volume was 40 μl.

The three cartridge designs were tested for flow rate and residence time without coagulation to determine if the track designs were sufficient to provide the long residence time necessary for an APTT analysis. Results of these comparisons are set forth in Tables 2 and 3 below.

TABLE 2

Comparison of 225 mm Half Track and 305 mm Half Track

| | Average flow rate (μl/sec) | | |
|---|---|---|---|
| | Low HCT (20%) | Medium HCT (35%) | High HCT (50%) |
| 225 mm | .058 +/− .020 N = 2 | .028 +/− .010 N = 2 | .018 +/− .008 N = 2 |
| 305 mm | .058 +/− .017 N = 8 | .029 +/− .010 N = 8 | .015 +/− .009 N = 8 |

(Flow rates calculated every 10 mm of length into track and averaged; test done at 37° C.)

TABLE 3

Residence Time Information
Comparison of 225 mm Half Track and 305 mm Half Track

| | Residence Time (seconds) | | |
|---|---|---|---|
| | Low HCT (20%) | Medium HCT (35%) | High HCT (50%) |
| 225 mm | 212 +/− 43.1 N = 2 | 430 +/− 59 N = 2 | 773 N = 1 |
| 305 mm | 453 +/− 77.2 N = 8 | 870 +/− 120 N = 8 | 1928 +/− 203 N = 4 |
| 305 mm time / 225 mm time = | 2.1 | 2.0 | 2.5 |

As shown in Table 2, by increasing the rate at which the radius of the track increases with distance from the reagent chamber, it was possible to increase the track length by more than ⅓ without decreasing the flow rate to an unacceptable level. In addition, Table 3 shows that the same increase in track length of about ⅓ resulted in a greater than 2 fold increase in the available residence time before sample reached the end of the track. This example demonstrates that it is possible to provide a track of sufficient length to allow a useful APTT analysis in a cartridge that requires only a single drop of blood. As shown in the empirical data for track volumes earlier in this example, all of the tracks provide volumes in the desirable range.

The improvement in residence time obtained by changing from a full circular cross section to a semicircular cross section can be seen by a comparison of data obtained from cartridges 1 and 2. This data is summarized in Table 4 below.

TABLE 4

Comparison of Full Track and Half Track Cartridges

| | Sample Residence Time (sec to end of track) | |
|---|---|---|
| | Low HCT (20%) | High HCT (50%) |
| Full Track (225 mm) | 143 | 525 |
| Half Track (225 mm) | 236 | 673 |
| Half Track / Full Track | 1.3 | 1.3 |

Residence time was increased by 30% by transition from a full track to a half track without requiring an increase in track length. Again, this information demonstrates the feasibility of providing for greater residence time in a single drop of blood by proper design of the capillary flow unit.

EXAMPLE 2

Balancing Reagents to Minimize Hematocrit Effects

Initial studies using a cartridge prepared essentially as shown in FIG. 1 and containing a capillary flow unit as described for cartridge 3 of Example 1 above showed a variation in APTT time with hematocrit (HCT). See Tables 3 and 4 above. Further studies were undertaken to eliminate this effect.

Different amounts of sulfatide activator (Purified Bovine MW≅890; Life Sciences, Inc.) were used with a constant amount of phosphatide mixture Soy lecithin Type II S (Sigma Chemical Co.; 2.24 mg/ml) and different amounts of phosphate mixture (Soy lecithin Type II S) were used with a constant amount of sulfatide (Purified Bovine MW≅890; 0.8 mM) in the reagent chamber of the cartridge as shown in Table 5 below. High HCT (46%) and low HCT (25%) samples were run for each reagent ratio in a cartridge. Results are set forth in Table 5.

TABLE 5

| Sulfatide Concentration* (mM) | APTT (seconds) Low HCT 25% | High HCT 46% | Difference |
|---|---|---|---|
| 0.4 | 56.1 | 52.6 | 3.5 |
| 0.8 | 58.0 | 57.5 | 0.5 |
| 1.2 | 59.0 | 58.9 | 0.1 |
| 1.6 | 63.1 | 62.4 | 0.8 |
| **Phosphatide Concentration* (mg/ml)** | **APTT (seconds) Low HCT** | **High HCT** | **Difference** |
| 0.56 | 61.2 | 62.9 | 1.7 |
| 1.12 | 57.8 | 58.0 | 0.2 |
| 2.24 | 58.0 | 57.5 | 0.5 |
| 4.48 | 61.8 | 59.6 | 2.2 |

*Reagent applied as 3 μl of liquid formulation at indicated concentration to reagent chamber and dried before use.

As shown in Table 5, it is possible to optimize the concentration of the sulfatide and the phosphatide mixture to obtain a reagent composition (0.8 mM sulfatide, 1.12 mg/ml phosphatide mixture) that is essentially independent of hematocrit.

EXAMPLE 3

Investigation of Sensitivity of APTT Measurement to Heparin Concentration

Blood sample were drawn from 20 normal donors using a butterfly apparatus. Blood was aspirated into syringes containing zero, low, and high quantities of heparin. Blood volumes drawn resulted in whole blood heparin concentrations of about 0.1 U/ml (low heparin) and 0.3 U/ml (high heparin). Equivalent plasma levels would be about 0.2 and 0.5 U/ml. Samples were applied to the cartridge of Example 2 prepared using the exemplary reagent formulation set forth in Table 1.

TABLE 6

| | | Heparin concentration | | |
|---|---|---|---|---|
| | HCT | zero | low | high |
| Patient No. | % | Cartridge APTT (seconds) | | |
| 1 | 44 | 65.7 | 88.55 | 129.25 |
| 2 | 43.5 | 63.6 | 81 | 184.3 |
| 3 | 37 | 64.75 | 80.85 | 130.55 |
| 4 | 35 | 62.25 | 76.05 | 108.35 |
| 5 | 39 | 60 | 103.45 | 144.85 |
| 6 | 44 | 63.8 | 97.85 | 183.35 |

TABLE 6-continued

| Patient No. | HCT % | Heparin concentration zero | low | high |
|---|---|---|---|---|
| | | Cartridge APTT (seconds) | | |
| 7 | 42.5 | 64.1 | 84.4 | 117.15 |
| 8 | 46.5 | 64.8 | 108.35 | 183.45 |
| 9 | 36 | 62.95 | 74.05 | 110.95 |
| 10 | 36.5 | 61.1 | 83.7 | 108.3 |
| 11 | 47.5 | 68.6 | 105.05 | 193 |
| 12 | 38 | 61.15 | 77.25 | 118.95 |
| 13 | 40 | 62.9 | 83.6 | 119.9 |
| 14 | 45 | 63.1 | 92.35 | 170.45 |
| 15 | 40 | 63.45 | 72.85 | 99.45 |
| 16 | 45 | 67.75 | 99.4 | 163.15 |
| 17 | 43.5 | 51.25 | 78 | 141.55 |
| 18 | 45 | 67 | 101.8 | 171.7 |
| 19 | 43 | 69.2 | 95.45 | 140.35 |
| 20 | 42.5 | 66.95 | 83.05 | 113.7 |

The data shown in Table 6 is raw data (i.e., actual clotting times in the cartridges as described above). This data can be converted to APTT values comparable to those obtained with any standard assay by correlating results obtained using the cartridge assay with the results obtained using the same samples in the other assay. Additionally, results can be correlated to particular conditions, such as heparin concentration or presence of a particular blood clotting factor, as is shown in the following example. As previously discussed, the values obtained for any particular APTT assay are normally independent of other APTT assays because of the lack of standardization in this field.

The APTT values from Table 6 were graphed against hematocrit to determine whether a correlation existed (no correlation was desired; i.e., correlation would have shown a dependence of APTT reading on hematocrit). No correlation was found.

EXAMPLE 4

Sensitivity of Cartridge APTT to Clotting Factor Deficiencies

Variation in sensitivity to clotting factor deficiencies for APTT reagents is well documented. It is important for the cartridge APTT assay to recognize deficiencies in the intrinsic coagulation pathway.

The cartridge APTT assay has been shown to be sensitive to deficiencies in Factors VIII, IX, XI, XII, prekallikrein, and kininogen. Factor sensitivity testing was performed using true deficient plasmas obtained from George King Bio-Medical Reagents (Indianapolis, Indiana). These citrated plasmas were mixed with fresh pooled plasma yielding neat plasma samples for measurement in the General Diagnostics APTT procedure. The same plasmas were mixed with fresh, washed O-negative blood cells, then recalcified immediately prior to measurement in the cartridge APTT system. Data show the cartridge system is generally more sensitive to changes in clotting factor deficiencies than the General Diagnostics system. Sensitivities are shown in Table 7 for both methods. Greater sensitivity is shown by a larger value for the APTT ratio.

TABLE 7

| Sample | % Factor Present | Factor Sensitivity APTT Ratio* Reference | Biotrack |
|---|---|---|---|
| Normal | 100 | 1.00 | 1.00 |
| Factor VIII | 50 | 1.24 | 1.55 |
| Deficient | 30 | 1.40 | 1.82 |
| | 10 | 1.74 | 2.52 |
| Factor IX | 50 | 1.08 | 1.16 |
| Deficient | 30 | 1.15 | 1.42 |
| | 10 | 1.33 | 1.76 |
| Factor XII | 50 | 1.17 | 1.45 |
| Deficient | 30 | 1.32 | 1.72 |
| | 10 | 1.64 | 2.38 |
| Factor XII | 50 | 1.00 | 1.13 |
| Deficient | 30 | 1.06 | 1.28 |
| | 10 | 1.21 | 1.85 |
| Prekallikrein Deficient | 44 | 1.08 | 1.32 |
| Kininogen | 50 | 1.20 | 1.67 |
| Deficient | 30 | 1.32 | 1.98 |

$$*\text{Ratio} = \frac{\text{APTT Result (sec) Factor Deficient Sample}}{\text{APTT Result (sec) Normal Sample Pool}}$$

All publication and patent applications mentioned in this specification are indicative of level of skill of those skilled in the art to which this invention pertains and are herein incorporated by reference to the same extent as if each individual patent application and publication had been individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. In a method for determining activated partial thromboplastin time in a fluid medium employing a device comprising, in a housing, a continuous capillary track comprising an inlet port, at least one capillary unit acting as the motive force for moving the fluid medium in the device, and a venting port, wherein said capillary track further contains a reagent capable of initiating blood clotting, and in which a blood sample is introduced into said entry port, said sample is allowed to transit said capillary track by capillary action, and said activated partial thromboplastin time is determined from the time required for blood coagulation and flow stoppage in said capillary track, the improvement that comprises:

utilizing as said reagent a mixture of (1) an activating agent for activated partial thromboplastin time measurements wherein said activating agent is a sulfatide or sulfoglycosylsphingolipid and (2) a phospholipid component, said activating agent and said phospholipid component being provided in amounts sufficient to initiate clotting, and to provide a time of flow stoppage that is essentially independent of blood hematocrit.

2. The method of claim 1, wherein said phospholipid component comprises a compound selected from the group consisting of soybean phospholipid type II-S, rabbit brain cephalin, rabbit lung cephalin, human brain cephalin, and a mammalian platelet extract.

3. The method of claim 1, further comprising providing said capillary track to allow continuous flow of whole blood in said capillary track in the absence of said reagent for at least 200 seconds.

4. The method of claim 3, wherein said continuous flow is achieved using no more than 40 μl of sample.

5. The method of claim 1, wherein said capillary track comprises a reagent unit and a capillary flow unit exiting said reagent unit.

6. The method of claim 5, wherein at least a portion of said capillary flow unit has a cross sectional area that increases with increasing distance from said reagent unit.

7. The method of claim 5, wherein said capillary flow unit has an initial cross sectional area of no more than 0.05 $mm^2$.

8. The method of claim 1, wherein said blood sample is whole blood.

9. The method of claim 8, wherein no chemical treatment of said blood takes place between obtaining said blood from a subject and applying said blood to said inlet port.

10. The method of claim 8, wherein movement of red blood cells past a point in said capillary track is detected by measurement of light scatter.

11. The method of claim 8, wherein said blood sample is capillary blood.

12. The method of claim 11, wherein said blood sample has a volume of no more than about 40 μl.

13. In a device for determining activated partial thromboplastin time comprising, in a housing, a continuous capillary track comprising an inlet port, at least one capillary unit acting as the motive force for moving the fluid medium in the device, and a venting port, wherein said capillary track further contains a reagent capable of initiating blood clotting, and in which a blood sample is introduced into said entry port, said sample is allowed to transit said capillary track by capillary action, and said activated partial thromboplastin time is determined from the time required for blood coagulation and flow stoppage in said capillary track, the improvement that comprises:

provided as said reagent a mixture of (1) an activating agent for activated prothrombin time measurements wherein said activating agent is a sulfatide or sulfoglycosylsphingolipid and (2) a phospholipid component, said activating agent and said phospholipid component being provided in amounts sufficient to initiate blood clotting, and to provide a time of flow stoppage that is essentially independent of blood hematocrit.

14. The device of claim 13, wherein said phospholipid component comprises a compound selected from the group consisting of soybean phospholipid type II-S, rabbit brain cephalin, rabbit lung cephalin, human brain cephalin, and mammalian platelet extract.

15. The device of claim 13, wherein said capillary track allows continuous flow of whole blood in said capillary track in the absence of said reagent for at least 200 seconds.

16. The device of claim 15, wherein said continuous flow is achieved using no more than 40 μl of sample.

17. The device of claim 13, wherein said capillary track comprises a reagent unit and a capillary flow unit exiting said reagent unit.

18. The device of claim 17, wherein at least a portion of said capillary flow unit has a cross sectional area that increases with increasing distance from said reagent unit.

19. The device of claim 17, wherein said capillary flow unit has a initial cross sectional area of no more than 0.05 $mm^2$.

20. The device of claim 13, wherein said device comprises first and second plastic plates welded together and said capillary track is formed between said plates and comprises a depression in a welded surface of said first plate, the second plate being flat at the location of said capillary track.

21. The device of claim 20, wherein said depression is substantially semicircular in the region of said capillary flow unit.

22. A capillary flow device capable of being used in an analysis for activated partial thromboplastin time, comprising:

a housing containing:

a continuous capillary pathway comprising an entry port, a first capillary unit, a reagent chamber, a second capillary unit, and a venting port; and a reagent in said reagent chamber, wherein:

(1) said first capillary unit comprises a capillary channel from 5 to 15 mm in length and having a width in the range of from 0.75 to 2 mm, and a height in the range of from 0.05 to 0.125 mm;

(2) said reagent chamber comprises a capillary chamber having a length in the range of from 5 to 15 mm, a width in the range of from 3 to 8 mm, and a height in the range of from 0.05 to 0.125 mm;

(3) said second capillary unit comprises a capillary channel having an initial radius in the range of from 0.05 to 0.175 mm and a final radius that provides capillary flow for a blood sample, said channel having one flat side, the remaining sides of said channel being formed by flat surfaces or curved surfaces joined without forming angles, all curved surfaces being convex relative to said flat side, wherein at least a portion of said second capillary increases in effective diameter with increasing distance from said reagent chamber;

(4) said reagent comprises an activator for activated partial thromboplastin time wherein said activator is a sulfatide or sulfoglycosylsphingolipid and a phospholipid component said activator and said phospholipid component being provided in amounts sufficient to initiate blood clotting and to provide a time of flow stoppage that is essentially independent of blood hematocrit clotting; and (5) said capillary track having a total volume in the range of from 20 to 100 μl.

23. The device of claim 22, wherein said second capillary unit has a volume of no more than 40 μl.

24. The device of claim 22, wherein said second capillary unit has a volume of no more than 25 μl.

25. The device of claim 22, wherein said housing comprises at least two plastic, pieces joined together and said second capillary unit is formed between a first plastic piece that is flat in the region of said second capillary unit and a second plastic piece that has a semicircular depression in the region of said second capillary unit.

26. The device of claim 25, wherein said semicircular depression has a constant radius for a first portion of said capillary unit.

27. The device of claim 26, wherein said semicircular depression has a radius that increases in a second portion following said initial portion.

28. The device of claim 27, wherein said second portion has a radius that increases with a decreasing rate of increase.

* * * * *